(12) United States Patent
Abele et al.

(10) Patent No.: US 6,277,084 B1
(45) Date of Patent: *Aug. 21, 2001

(54) ULTRASONIC MEDICAL DEVICE

(75) Inventors: John E. Abele, Concord; Kevin R. Heath, Weston, both of MA (US)

(73) Assignee: Boston Scientific Corporation, Natick, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/851,163

(22) Filed: May 5, 1997

Related U.S. Application Data

(63) Continuation of application No. 08/756,187, filed on Nov. 25, 1996, now abandoned, which is a continuation of application No. 08/527,749, filed on Sep. 13, 1995, now abandoned, which is a continuation of application No. 07/861,253, filed on Mar. 31, 1992, now abandoned.

(51) Int. Cl.$^7$ .................................................... A61B 17/22
(52) U.S. Cl. .............................. 601/2; 606/127; 606/169; 606/171; 29/270
(58) Field of Search ................................ 606/127, 31, 27, 606/171, 159, 169, 128; 600/585, 461; 607/96; 604/22; 601/2; 428/364, 375, 378, 379, 386, 389, 397; 29/592.1, 729, 758, 270

(56) References Cited

U.S. PATENT DOCUMENTS

| | | |
|---|---|---|
| 2,524,661 | 10/1950 | Harder et al. . |
| 3,196,876 | 7/1965 | Miller . |
| 3,335,443 | 8/1967 | Parisi et al. . |
| 3,466,166 | 9/1969 | Levinstein et al. . |
| 3,528,410 | 9/1970 | Banko . |
| 3,558,066 | 1/1971 | Alliger . |
| 3,562,024 | 2/1971 | Smith et al. . |

(List continued on next page.)

FOREIGN PATENT DOCUMENTS

| | | |
|---|---|---|
| 1324533 | 11/1993 | (CA) . |
| 33 29 176 | 11/1984 | (DE) . |
| 40 22 956 | 2/1992 | (DE) . |
| 92 06 170 | 5/1992 | (DE) . |
| 0 067 929 | 12/1982 | (EP) . |
| 0 121 447 | 10/1984 | (EP) . |
| 0 221 570 | 5/1987 | (EP) . |

(List continued on next page.)

OTHER PUBLICATIONS

DFT Drawn Filled Tubing (1988).
ASTM Standards 1991 Annual Book, vol. 13.01 Medical Devices.
Assefpour–Dezfuly et al., Journal of Materials Science, Nov. 1983, pp. 2815–2936.
Klinger and Kurisky, "MP35N alloy—the ultimate wire material", *Wire Journal*, 1980.
Metals Handbook, Tenth Edition, vol. 1, ASM International, Materials Park, OH 1990.
Schneider, PCT/US93/11262 Search Report, Nov. 1993.
Schneider, PCT/IB95/00253 Search Report, Oct. 1995.

(List continued on next page.)

*Primary Examiner*—Brian L. Casler
(74) *Attorney, Agent, or Firm*—Fish & Richardson P.C.

(57) ABSTRACT

Wires are used for conducting ultrasound energy. These wires achieve optimum properties by creating a multiple material coaxial construction. For example, in a particular embodiment it is desirable to have an elastic core (nitinol) for conducting axial vibrations (sonic or ultrasonic) and a thin stiff cladding (stainless steel) in order to minimize traverse vibrations which result in loss of energy.

43 Claims, 1 Drawing Sheet

U.S. PATENT DOCUMENTS

| | | |
|---|---|---|
| 3,584,327 * | 6/1971 | Murry ............................................ 601/2 |
| 3,589,363 | 6/1971 | Banko et al. . |
| 3,605,750 | 9/1971 | Sheridan . |
| 3,618,594 | 11/1971 | Banko . |
| 3,618,614 | 11/1971 | Flynn . |
| 3,749,086 | 7/1973 | Kline et al. . |
| 3,805,787 * | 4/1974 | Banko ............................................ 601/2 |
| 3,823,717 | 7/1974 | Pohlman et al. . |
| 3,830,240 | 8/1974 | Antonevich et al. . |
| 3,861,391 | 1/1975 | Antonevich et al. . |
| 3,896,811 | 7/1975 | Storz . |
| 3,930,173 | 12/1975 | Banko . |
| 3,941,122 | 3/1976 | Jones . |
| 3,942,519 | 3/1976 | Shock . |
| 3,956,826 | 5/1976 | Perdeaux, Jr. . |
| 4,023,557 | 5/1977 | Thorne et al. . |
| 4,041,931 | 8/1977 | Elliott et al. . |
| 4,178,935 | 12/1979 | Gekhman et al. . |
| 4,188,952 | 2/1980 | Loschilov et al. . |
| 4,202,349 | 5/1980 | Jones . |
| 4,281,419 | 8/1981 | Treace . |
| 4,295,464 | 10/1981 | Shihata . |
| 4,345,602 | 8/1982 | Yoshimara et al. . |
| 4,351,326 | 9/1982 | Kosonen . |
| 4,370,131 | 1/1983 | Banko . |
| 4,380,574 | 4/1983 | Gessinger et al. . |
| 4,406,284 | 9/1983 | Banko . |
| 4,417,578 | 11/1983 | Banko . |
| 4,425,115 | 1/1984 | Wuchinich . |
| 4,425,908 | 1/1984 | Simon . |
| 4,428,379 * | 1/1984 | Robbins et al. ............................ 128/660 |
| 4,431,006 * | 2/1984 | Trimmer et al. ............................ 128/660 |
| 4,464,176 | 8/1984 | Wijayarathma . |
| 4,465,481 | 8/1984 | Blake . |
| 4,474,180 | 10/1984 | Angulo . |
| 4,486,680 | 12/1984 | Bonnet et al. . |
| 4,504,268 | 3/1985 | Herlitze . |
| 4,517,793 | 5/1985 | Carus . |
| 4,518,444 | 5/1985 | Albrecht et al. . |
| 4,535,759 * | 8/1985 | Polk et al. ..................................... 601/2 |
| 4,553,564 | 11/1985 | Maass et al. . |
| 4,561,438 | 12/1985 | Bonnet et al. . |
| 4,572,184 | 2/1986 | Stohl et al. . |
| 4,577,637 | 3/1986 | Mueller, Jr. . |
| 4,580,568 | 4/1986 | Gianturco . |
| 4,600,446 | 7/1986 | Torisaka et al. . |
| 4,602,633 | 7/1986 | Goodfriend et al. . |
| 4,615,331 | 10/1986 | Kramann . |
| 4,654,092 | 3/1987 | Melton . |
| 4,655,771 | 4/1987 | Wallsten . |
| 4,657,024 | 4/1987 | Coneys . |
| 4,681,110 | 7/1987 | Wikto . |
| 4,692,139 | 9/1987 | Stiles . |
| 4,697,595 | 10/1987 | Breyer et al. . |
| 4,698,058 | 10/1987 | Greenfeld et al. . |
| 4,706,681 | 11/1987 | Breyer et al. . |
| 4,719,916 | 1/1988 | Ravo . |
| 4,724,846 | 2/1988 | Evans, III . |
| 4,731,084 | 3/1988 | Dunn et al. . |
| 4,732,152 | 3/1988 | Wallsten . |
| 4,733,665 | 3/1988 | Palmaz . |
| 4,748,971 | 6/1988 | Borodulin et al. . |
| 4,748,986 | 6/1988 | Morrison et al. . |
| 4,750,488 | 6/1988 | Wuchinich et al. . |
| 4,750,902 | 6/1988 | Wuchinich et al. . |
| 4,751,916 | 6/1988 | Bory . |
| 4,760,849 | 8/1988 | Kropf . |
| 4,768,507 | 9/1988 | Fischell et al. . |
| 4,770,664 | 9/1988 | Gogolewski . |
| 4,771,773 | 9/1988 | Kropf . |
| 4,793,348 | 12/1988 | Palmaz . |
| 4,796,637 | 1/1989 | Mascuch et al. . |
| 4,800,890 | 1/1989 | Cramer . |
| 4,808,246 | 2/1989 | Albrecht et al. . |
| 4,816,018 | 3/1989 | Parisi . |
| 4,817,600 | 4/1989 | Herms et al. . |
| 4,819,618 | 4/1989 | Liprie . |
| 4,823,793 | 4/1989 | Angulo et al. . |
| 4,830,003 | 5/1989 | Wolff et al. . |
| 4,830,023 | 5/1989 | de Toledo et al. . |
| 4,830,262 | 5/1989 | Ishibe . |
| 4,834,747 | 5/1989 | Gogolewski . |
| 4,842,590 | 6/1989 | Tanabe et al. . |
| 4,846,186 | 7/1989 | Box et al. . |
| 4,848,343 | 7/1989 | Wallsten . |
| 4,848,348 | 7/1989 | Craighead . |
| 4,850,999 | 7/1989 | Planck . |
| 4,856,516 | 8/1989 | Hillstead . |
| 4,867,173 | 9/1989 | Leoni . |
| 4,870,953 | 10/1989 | DonMichael et al. . |
| 4,875,480 | 10/1989 | Imbert . |
| 4,883,486 | 11/1989 | Kapadia et al. . |
| 4,884,579 | 12/1989 | Engelson . |
| 4,886,062 | 12/1989 | Wiktor . |
| 4,899,733 | 2/1990 | DeCastro et al. . |
| 4,906,241 | 3/1990 | Noddin . |
| 4,907,572 | 3/1990 | Borodulin et al. . |
| 4,920,954 | 5/1990 | Alliger et al. . |
| 4,922,905 | 5/1990 | Strecker . |
| 4,922,924 | 5/1990 | Gambale et al. . |
| 4,925,445 | 5/1990 | Sakamoto et al. . |
| 4,932,419 | 6/1990 | de Toledo . |
| 4,934,380 | 6/1990 | de Toledo . |
| 4,936,845 | 6/1990 | Stevens . |
| 4,950,227 | 8/1990 | Savin et al. . |
| 4,953,553 | 9/1990 | Tremulis . |
| 4,954,126 | 9/1990 | Wallsten . |
| 4,957,110 | 9/1990 | Vogel et al. . |
| 4,964,409 | 10/1990 | Tremulis . |
| 4,969,891 | 11/1990 | Gewertz . |
| 4,971,490 | 11/1990 | Hawkins . |
| 4,980,964 | 1/1991 | Boeke . |
| 4,984,581 | 1/1991 | Stice . |
| 4,989,608 | 2/1991 | Ratner . |
| 4,990,151 | 2/1991 | Wallsten . |
| 4,995,878 | 2/1991 | Rai . |
| 5,001,825 | 3/1991 | Halpern . |
| 5,003,987 | 4/1991 | Grinwald . |
| 5,003,989 | 4/1991 | Taylor . |
| 5,012,797 * | 5/1991 | Liang et al. ................................ 601/2 |
| 5,015,183 | 5/1991 | Fenick . |
| 5,015,253 | 5/1991 | MacGregor . |
| 5,019,085 | 5/1991 | Hillstead . |
| 5,019,090 | 5/1991 | Pinchuk . |
| 5,024,232 | 6/1991 | Smid et al. . |
| 5,024,617 | 6/1991 | Karpiel . |
| 5,025,799 | 6/1991 | Wilson . |
| 5,026,377 | 6/1991 | Burton et al. . |
| 5,040,280 | 8/1991 | Takada . |
| 5,040,283 | 8/1991 | Pelgrom . |
| 5,047,050 | 9/1991 | Arpesani . |
| 5,052,407 | 10/1991 | Hauser et al. . |
| 5,059,166 | 10/1991 | Fischell et al. . |
| 5,061,275 | 10/1991 | Wallsten et al. . |
| 5,064,428 | 11/1991 | Cape et al. . |
| 5,064,435 | 11/1991 | Porter . |
| 5,069,217 | 12/1991 | Fleischacker, Jr. . |
| 5,069,226 | 12/1991 | Yamauchi et al. ....................... 128/772 |
| 5,071,407 | 12/1991 | Termin et al. . |
| 5,092,877 | 3/1992 | Pinchuk . |
| 5,095,915 | 3/1992 | Engelson . |

| | | |
|---|---|---|
| 5,104,404 | 4/1992 | Wolff. |
| 5,109,830 | 5/1992 | Cho. |
| 5,111,829 | 5/1992 | de Toledo. |
| 5,129,890 | 7/1992 | Bates et al.. |
| 5,139,480 | 8/1992 | Hickle et al.. |
| 5,147,317 | 9/1992 | Amplatz. |
| 5,147,385 | 9/1992 | Beck et al.. |
| 5,152,777 | 10/1992 | Goldberg. |
| 5,163,433 * | 11/1992 | Kagawa et al. .......................... 601/2 |
| 5,163,952 | 11/1992 | Froix. |
| 5,171,233 | 12/1992 | Amplatz. |
| 5,171,262 | 12/1992 | MacGregor. |
| 5,176,617 | 1/1993 | Fischell et al.. |
| 5,197,978 | 3/1993 | Hess. |
| 5,201,901 | 4/1993 | Harada et al.. |
| 5,207,706 | 5/1993 | Menaker. |
| 5,213,111 | 5/1993 | Cook et al.. |
| 5,217,483 | 6/1993 | Tower. |
| 5,248,296 * | 9/1993 | Alliger .................................. 609/22 |
| 5,256,158 | 10/1993 | Tolkoff et al.. |
| 5,256,764 | 10/1993 | Tang et al.. |
| 5,276,455 | 1/1994 | Fitzsimmons et al.. |
| 5,304,140 | 4/1994 | Kugo et al.. |
| 5,320,100 | 6/1994 | Herweck et al.. |
| 5,334,201 | 8/1994 | Cowan. |
| 5,354,309 | 10/1994 | Schnepp-Pesch et al.. |
| 5,360,442 | 11/1994 | Dahl et al.. |
| 5,366,504 | 11/1994 | Andersen et al.. |
| 5,368,661 | 11/1994 | Nakamura et al.. |
| 5,374,261 | 12/1994 | Yoon. |
| 5,382,259 | 1/1995 | Phelps et al.. |
| 5,389,106 | 2/1995 | Tower. |
| 5,397,293 * | 3/1995 | Alliger .................................. 601/2 |
| 5,474,563 | 12/1995 | Myler et al.. |
| 5,476,508 | 12/1995 | Amstrup. |
| 5,489,277 | 2/1996 | Tolkoff et al.. |
| 5,496,330 | 3/1996 | Bates. |
| 5,498,236 * | 3/1996 | Dubrul et al. .......................... 604/22 |
| 5,514,154 | 5/1996 | Lau et al.. |
| 5,556,413 | 9/1996 | Lam. |
| 5,609,629 | 3/1997 | Fearnot et al.. |
| 5,628,787 | 5/1997 | Mayer. |
| 5,630,840 | 5/1997 | Mayer. |
| 5,658,296 | 8/1997 | Bates. |
| 5,725,549 | 3/1998 | Lam. |
| 5,725,570 | 3/1998 | Heath. |
| 5,733,326 | 3/1998 | Tomonto et al.. |
| 5,843,163 | 12/1998 | Wall. |
| 5,858,556 | 1/1999 | Eckert et al.. |
| 5,879,382 | 3/1999 | Boneau. |
| 5,902,332 | 5/1999 | Schatz. |
| B1 4,655,771 | 9/1996 | Wallsten. |
| B1 4,954,126 | 5/1996 | Wallsten. |
| B1 5,197,978 | 5/1996 | Hess. |

FOREIGN PATENT DOCUMENTS

| | | |
|---|---|---|
| 0 405 429 A2 | 1/1991 | (EP). |
| 0 405 823 A2 | 1/1991 | (EP). |
| 0 433 011 | 6/1991 | (EP). |
| 0 435 518 | 7/1991 | (EP). |
| 0 042 703 A1 | 12/1991 | (EP). |
| 0 481 365 | 4/1992 | (EP). |
| 0 547 739 | 6/1993 | (EP). |
| 0 556 940 A1 | 8/1993 | (EP). |
| 0 593 163 A1 | 4/1994 | (EP). |
| 2 479 685 | 3/1981 | (FR). |
| 1 205 743 | 9/1970 | (GB). |
| 2 195 257 | 4/1988 | (GB). |
| 59-19958 | 2/1978 | (JP). |
| 1-259541 | 10/1989 | (JP). |
| WO 88/01924 | 3/1988 | (WO). |
| WO 90/01300 | 2/1990 | (WO). |
| WO 91/04716 | 4/1991 | (WO). |
| WO 91/19528 | 12/1991 | (WO). |
| WO 92/11815 | 7/1992 | (WO). |
| WO 92/13483 | 8/1992 | (WO). |
| WO 92/19310 | 11/1992 | (WO). |
| WO 92/21399 | 12/1992 | (WO). |
| WO 93/19803 | 10/1993 | (WO). |
| WO 93/19804 | 10/1993 | (WO). |
| WO 94/16646 | 8/1994 | (WO). |
| WO 94/24961 | 11/1994 | (WO). |
| WO 97/04895 | 2/1997 | (WO). |

OTHER PUBLICATIONS

Sigwart et al., *The New England Journal of Medicine*, vol. 316, Mar. 19, 1987.

*Alliger, "Ultrasonic Disruption", Am. Lab. (a journal), vol. 7, No. 10, 1975, pp. 75–76, 78, 80–82, 84 and 85.

*Alliger et al., "Tumoricidal Effect of a New Ultrasonic Needle", Federation Proceedings—Abstracts, vol. 44, No. 4, Mar. 5, 1985, p. 1145.

*Ariani et al., "Dissolution of Peripheral Arterial Thrombi by Ultrasound", Circulation (American Heart Association), vol. 84, No. 4, Oct. 1991, pp. 1680–1688.

*Chae et al., "Ultrasonic Dissolution of Human Thrombi", Journal of the American College of Cardiology, vol. 15, No. 7, Jun. 1990, p. 64A.

*Chaussy et al., "Transurethral Ultrasonic Ureterolithotripsy Using a Solid–Wire Probe", Urology, vol. XXIX, No. 5, May 1987, pp. 531–532.

*Chaussy et al., "Transurethral Ultrasonic Uretero–lithotripsy: A New Technique", The Journal of Radiology, vol. 137, No. 4, Part 2, Apr. 1987, p. 159A.

*Demer et al., "High Intensity Ultrasound Increases Distensibility of Calcific Atherosclerotic Arteries", Journal of the American College of Cardiology, vol. 18, No. 5, Nov. 1, 1991, pp. 1259–1262.

*Ernst et al., "Ability of High–Intensity Ultrasound to Ablate Human Artherosclerotic Plaques and Minimize Debris Size", The American Journal of Cardiology, vol. 68, No. 2, Jul. 15, 1991, pp. 242–246.

*Freeman et al., "Ultrasonic Angioplasty Using a New Flexible Wire System", Journal of the American College of Cardiology, vol. 13, No. 1, Jan. 1989, p. 4A.

*Freeman et al., "Ultrasonic Energy Produces Endothelium––Dependent Vasomotor Relaxation in Vitro", Clinical Research–Official Publication of the Amer. Federation for Clin. Research, vol. 36, No. 5, Sep. 1988, p. 786A.

*Goodfriend, "Ultrasonic Ureterolithotripsy Employed in a Flexible Ureteroscope", The Journal of Urology, vol. 139, No. 4, Part 2, Apr. 1988, p. 282A.

*Goodfriend, "Ultrasonic and Electrohydraulic Lithotripsy of Ureteral Calculi", Urology, vol. XXIII, No. 1, Jan. 1984, pp. 5–8.

*Goodfriend, "Transvesical Intussusception Ureterectomy", Urology, vol. XXI, No. 4, Apr. 1983, pp. 414–415.

*Goodfriend, "Disintegration of Ureteral Calculi by Ultrasound", Urology, vol. 1, No. 3, Mar. 1973, pp. 260–263.

*Hong et al., "Ultrasonic clot disruption: An in vitro study", American Heart Journal, vol. 20, No. 2, Aug. 1990, pp. 418–422.

*Hunter et al., "Transurethral Ultrasonic: Uretero–lithotripsy", The Journal of Urology, vol. 135, No. 4, Part 2, Apr. 1986, p. 299A.

*Marco et al., "Intracoronary Ultra Sound Imaging: Preliminary Clinical Results", European Heart Journal–Journal of the European Society of Cardiology–Abstract Supplement (Academic Press), Aug. 1990, p. 190.

*Monteverde et al., "Ultrasound Arterial Recanalization in Acute Myocardial Infarction", Supplement to Circulation (American Heart Association), vol. 82, No. 4, Oct. 1990, pp. III–622.

*Monteverde et al., "Percutaneous Transluminal Ultrasonic Angioplasty in Totally Occluded Peripheral Arteries: Imm.&Intermed.Clinical Results", Suppl. to Circ. (Am. Hrt. Assoc.), 82:4, Oct. 1990, pp. III–678.

*Rosenschein et al., "Clinical Experience with Ultrasonic Angioplasty of Totally Occluded Peripheral Arteries", Journal of the Am. College of Cardiology, vol. 15, No. 1, Jan. 1990, p. 104A.

*Siegel et al., "In Vivo Ultrasound Arterial Recanalization of Atherosclerotic Total Occlusions", Journ. of the American College of Cardiology, vol. 15, No. 2, Feb. 1990, pp. 345–351.

*Siegel et al., "Percutaneous Ultrasonic Angioplasty: Initial Clinical Experience", The Lancet, vol. II, No. 8666, Sep. 30, 1989, pp. 772–774.

*Siegel et al., "Ultrasonic Plaque Ablation—A New Method for Recanalization of Partially or Totally Occluded Arteries", Circulation, vol. 78, No. 6, Dec. 1988, pp. 1443–1448.

* cited by examiner

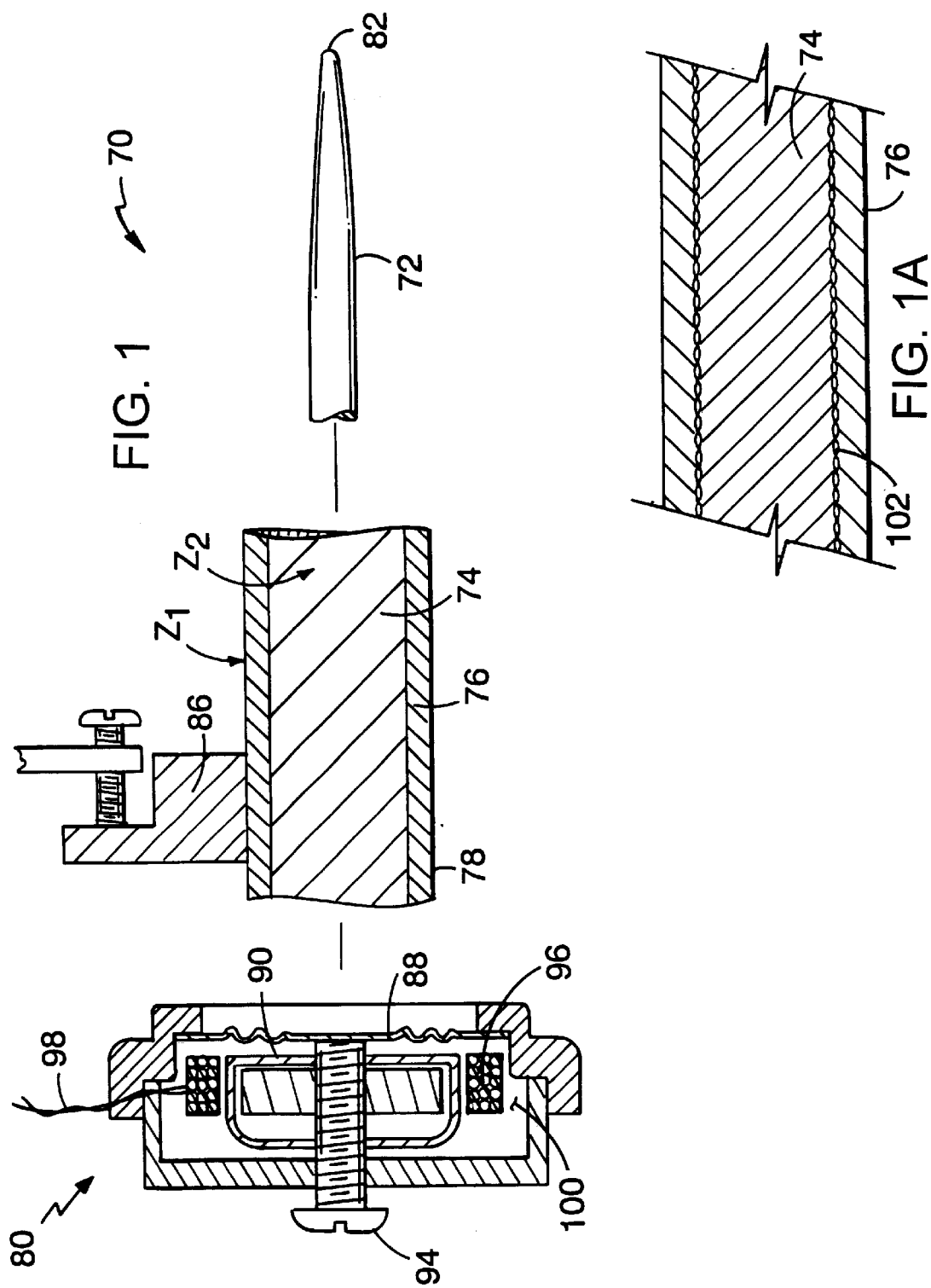

ULTRASONIC MEDICAL DEVICE

RELATED APPLICATION

This is a continuation of U.S. Ser. No. 08/756,187 filed Nov. 25, 1996 now abandoned, which is a continuation of U.S. Ser. No. 08/527,749 filed Sep. 13, 1995 now abandoned, which is a continuation of U.S. Ser .No. 07/861,253, filed Mar. 31, 1992, now abandoned.

FIELD OF THE INVENTION

This invention relates to an ultrasound medical device. Noninvasive medical procedures reduce the risk of surgery by introducing medical devices to a body cavity through small incisions or body orifices. The devices are carefully designed so that they may be controlled from the proximal end remaining outside the body to carry out the requirement treatment at the desired location inside the body.

SUMMARY OF THE INVENTION

In one aspect, the invention features a medical device having at least a portion (e.g., an elongated wire-form or draw-form wire) for use within the body. The portion includes an extended metal outer member having an exposed outer surface and a core within the outer member formed of a metal different than the metal of the outer member. The core is secured within and substantially enclosed by the outer member. The portion is in the form of an ultrasonic probe. In embodiments, for example, the probe is an elastic probe having a titanium core and nitinol outer member. The outer member and the core are constructed of materials of substantially different acoustic impedance. The acoustic energy is provided by axial excitation.

The invention features wires (e.g., elongated wire-forms or draw-form wires) that can be used for conducting ultrasound energy. These wires achieve optimum properties by creating a multiple material coaxial construction. For example, in a particular embodiment it is desirable to have an elastic core (nitinol) for conducting axial vibrations (sonic or ultrasonic) and a thin stiff cladding (stainless steel) in order to minimize traverse vibrations which result in loss of energy.

The term "metal" as used herein includes electropositive chemical elements characterized by ductility, malleability, luster, and conductivity of heat and electricity, which can replace the hydrogen of an acid and forms bases with the hydroxyl radical and including mixtures including these elements and alloys. Many examples are given below.

Further aspects feature and advantages follow.

DESCRIPTION OF THE PREFERRED EMBODIMENTS(S)

We first briefly describe the drawings.

DRAWINGS

FIG. 1 is a schematic illustration of an ultrasound wire device of the invention and FIG. 1a is longitudinal cross-sectional view of a portion of another embodiment of an ultrasound device, having air-filled microspheres (shown greatly enlarged) at the interface of the core and outer member.

DESCRIPTION

Referring to FIGS. 1 and 1a, an ultrasound device 70 is shown to include a wire 72 including an inner core 74 and an outer member 76. The wire 72 extends from a proximal end 78, attached to an ultrasound source mechanism 80, to a distal end 82 which is positioned at a location where ultrasound energy is to be delivered. Briefly, the source 80 includes a clamping mechanism 86 to couple the core near the distal end 78 of the wire to a diaphragm 88 which is vibrated ultrasonically by a piston transducer 90. The transducer 90 includes a phosphorous-bronze bell 92 whose tension may be adjusted by screw member 94. The magnetic field from coils 96 cause the transducer to vibrate when electrical energy is supplied through leads 98. Cooling vents 100 surround the coils 98. Ultrasound energy supplied by the mechanism 80 to the core at the proximal portion 78 of the wire is transmitted through the core to the distal end 82 where it can be utilized to treat tissue.

Referring to FIG. 1a, in some embodiments, the core 74 is bonded to the outer member 76 at intermittent points, leaving therebetween air-filled microspheres 102 which impede the transmission of ultrasound energy laterally. The microspheres could be produced by machining grooves into the core or outer member before assembly.

By proper selection of the outer and core metals enhanced transmission of ultrasound energy through the core may be achieved while minimizing lateral mode losses through the outer material. Preferably, the metals are selected based on their acoustic impedance ($Z_1$, $Z_2$) to induce internal reflection of acoustic waves propagating off axis. An advantage of the system is that lower power may be applied so that the transmission system operates at lower temperature. The outer member can further be selected to reduce vibration. A preferred embodiment of an elastic probe employs high acoustic transmitting titanium at the core and nitinol as the outer member. In another embodiment, the core member may be for example, nitinol and the outer member stainless steel. In another embodiment, the core is tantalum. The outer member could also be formed of a non-metal, e.g., carbon or glass. The ultrasound energy could be used to ablate tissue, enhance delivery of drugs and induce relaxation of tissue, e.g., tumors and in eye surgery e.g., to dissolve cataracts. The acoustic energy can be provided to the probe by axial excitation as illustrated above or by torsional excitation or a combination thereof. Preferably, the outer member is formed of a continuous solid mass of a highly elastic biocompatible metal.

Superelastic or pseudo-elastic metal alloys include, for example, a nitinol (e.g., 55% nickel, 45% titanium). Other examples of superelastic materials include, e.g., Silver-Cadmium (Ag—Cd), Gold-Cadmium (Au—Cd), Gold-Copper-Zinc (Au—Cu—Zn), Copper-Aluminum-Nickel (Cu—Al—Ni), Copper-Gold-Zinc (Cu—Au—Zn), Copper-Zinc (Cu—Zn), Copper-Zinc-aluminum (Cu—Zn—Al), Copper-Zinc-Tin (Cu—Zn—Sn), Copper-Zinc-Xenon (Cu—Zn—Xe), Iron Beryllium ($Fe_3Be$), Iron Platinum ($Fe_3Pt$), Indium-Thallium (In—Tl), iron-manganese (Fe—Mn) Nickel-Titanium-Vanadium (Ni—Ti—V), Iron-Nickel-Titanium-Cobalt (Fe—Ni—Ti—Co) and Copper-Tin (Cu—Sn). See Schetsky, L. McDonald, "Shape Memory Alloys", *Encyclopedia of Chemical Technology* (3rd ed.), John Wiley & Sons, 1982, vol. 20. pp. 726–736 for a full discussion of superelastic alloys. Other examples of metals suitable for the outer member include stainless steel, titanium and various alloys of these metals and the precursor of superelastic alloys. Precursors of superelastic alloys are those alloys which have the same chemical constituents as superelastic alloys, but have not been processed to impart the superelastic property. Such alloys are further described in co-owned and co-pending U.S. Ser. No. 07/507,375, filed Apr. 10, 1990, the entire contents of which is hereby incorporated by reference.

The outer member and core may be in many cross-sectional geometric configurations, such as circular, square, triangular, hexagonal, octagonal, trapezoidal and the geometrical configuration of the core may differ from that of the longitudinal member. For example, the wire may be rectangular in cross-section with a rectangular core or triangular or hexagonal in cross-section with a circular core. The wire may also take on the form of tubing with a lumen within the core extending along the axis of the wire. The wire may also include successive layers of different metals to form a composite system. The core may extend intermittently along the axis in a desired pattern.

The medical device may be formed, for example, by drilling a relatively large rod of the outer member material to form a lumen, positioning a rod of core material in the lumen, sealing the ends of the lumen, e.g., by crimping and drawing as known in the art, through a series of dies of decreasing diameter until the desired outer diameter is achieved. The device may be heat treated to anneal, harden or impart superelastic properties. Other methods of formation may be, e.g., by coating the core with the desired outer material such as by electro- or electroless plating. The materials used in the outer member and core are also selected based on their workability for forming the wire, including factors such as machinability, for forming the longitudinal member into a tubular piece and the core member into a rod shaped piece, stability in gaseous environments at annealing temperatures, properties related to welding, drawing, forging, swaging, the ability to accept coatings such as adhesives, polymers, lubricants and practical aspects such as cost and availability.

An example is given below in which the wire has a tantalum core and a nitinol outer member.

EXAMPLE 1

A 500 foot length of wire (0.0052 inch in diameter) having an outer member formed of a precursor of a nitinol (55% Ni/45% Ti) superelastic alloy and a core material of tantalum (0.00175 inch in diameter) is formed by drilling a 0.25 inch diameter bore in a 0.75 inch rod of the outer member material and providing in the drilled lumen a tantalum member of substantially matched outer diameter. The rod is mechanically forged in a standard hot forging and rolling apparatus, then hammered such that no substantial voids between the core and outer longitudinal member are present. One end of the rod is sealed and the opposite end is cold drawn longitudinally through a dye to the final diameter of about 0.038 inch, with a core diameter of 0.0052 inch. Initially, the outer member of the wire is the precursor of a superelastic alloy, i.e., it has not been heat treated to impart the superelastic property. The wire may be annealed at 460° C. for 3 to 15 minutes, to induce the superelastic nature of the wire.

Other embodiments are in the following claims.

What is claimed is:

1. An ultrasound medical device comprising:
    a source of ultrasound energy, and an elongated wire-form for transmission of ultrasound energy, said wire-form having a proximal portion, a distal portion, and a length therebetween, said wire-form including along its length a sheath surrounding and contacting a metal core where said sheath and said metal core are formed of different materials, wherein said core and said sheath are bonded at points where said core contacts said sheath.

2. The medical device of claim 1 wherein the wire-form is a draw-form.

3. The medical device of claim 1 wherein said sheath and core are constructed of materials of substantially different ultrasound impedance.

4. The medical device of claim 1 wherein said core and said sheath are different metals.

5. The medical device of claim 1 including air pockets disposed between said points where said core is bonded to said sheath.

6. The medical device of claim 1 wherein said core has a circular cross-section.

7. The medical device of claim 1 wherein said source of ultrasound energy provides axial excitation.

8. The medical device of claim 1 wherein said source of ultrasound energy is coupled to said core.

9. The medical device of claim 1 wherein said source of ultrasound energy and said wire-form are arranged for ablation of tissue.

10. The ultrasound medical device of claim 1, wherein said sheath is formed of nitinol and said core is formed of titanium.

11. The ultrasound medical device of claim 1, wherein said sheath is formed of stainless steel and said core is formed of a nitinol.

12. The ultrasound medical device of claim 1, wherein said sheath is formed of a non-metal.

13. The ultrasound medical device of claim 1, wherein said core is formed of tantalum.

14. The ultrasound medical device of claim 1, wherein said sheath is formed of a nitinol and said core is formed of tantalum.

15. A method of transmitting ultrasound energy into the body comprising:
    providing a source of ultrasound energy,
    coupling said source of ultrasound energy to an elongated wire-form for use within the body, said wire-form having a proximal portion, distal portion, and a length therebetween, said wire-form including along its length a sheath surrounding and contacting a metal core where said sheath and said core are formed of different materials, said core and sheath being bonded at intermittent points corresponding to points where said core contacts said sheath,
    generating ultrasound energy with said source of ultrasound energy, and
    transmitting said ultrasound energy along said length of said wire form.

16. The method of claim 15 comprising transmitting said ultrasound energy from the proximal end to the distal end and utilizing said ultrasound energy at the distal end to treat tissue.

17. The method of claim 16 comprising coupling said source of ultrasound energy to said core.

18. The method of claim 15 comprising ablating tissue with said ultrasound energy.

19. The method of claim 15 comprising relaxing tissue with said ultrasound energy.

20. The method of claim 15 comprising enhancing delivery of drug with said ultrasound energy.

21. The method of claim 15 wherein said wire-form is a draw-form.

22. The method of claim 15 wherein said sheath and core are constructed of materials of substantially different ultrasound impedance.

23. The method of claim 15 wherein said core and said sheath are different metals.

24. The method of claim 15 including air pockets disposed between said points where said sheath is bonded to said core.

25. The method of claim 15 wherein said core has a circular cross-section.

26. The method of claim 15 wherein said source of ultrasound energy provides axial excitation.

27. The method of claim 15, wherein said sheath is formed of nitinol and said core is formed of titanium.

28. The method of claim 15, wherein said sheath is formed of stainless steel and said core is formed of a nitinol.

29. The method of claim 15, wherein said sheath is formed of a non-metal.

30. The method of claim 15, wherein said core is formed of tantalum.

31. The method of claim 15, wherein said sheath is formed of a nitinol and said core is formed of tantalum.

32. A method for making an ultrasound medical device comprising:

providing a draw-form wire with a first material forming a sheath surrounding and contacting a second metal forming a core different than the first metal, said core and sheath being bonded at intermittent points corresponding to points where said core contacts said sheath, providing a source of ultrasound energy, and coupling said draw-form wire to said source of ultrasound energy.

33. The medical device of claim 32 wherein said sheath and core are constructed of materials of substantially different ultrasound impedance.

34. The method of claim 32 comprising coupling said source of ultrasound energy to said core.

35. The method of claim 32 including air pockets disposed between said points where said sheath is bonded to said core.

36. The method of claim 32 wherein said core has a circular cross-section.

37. The method of claim 32 wherein said source of ultrasound energy provides axial excitation.

38. The method of claim 32, wherein said sheath is formed of a nitinol and said core is formed of titanium.

39. The method of claim 32, wherein said sheath is formed of stainless steel and said core is formed of a nitinol.

40. The method of claim 32, wherein said sheath is formed of a non-metal.

41. The method of claim 32, wherein said core is formed of tantalum.

42. The method of claim 32, wherein said sheath is formed of nitinol and said core is formed of tantalum.

43. The method of claim 32 comprising transmitting said energy from a proximal end of the draw-form wire to a distal end of the draw-form wire and utilizing said energy at the distal end to treat tissue.

* * * * *